United States Patent
Damasco et al.

(10) Patent No.: US 9,326,808 B2
(45) Date of Patent: *May 3, 2016

(54) SYSTEM FOR PROVIDING COMPUTER GUIDED ABLATION OF TISSUE

(75) Inventors: Sanford D. Damasco, Irvine, CA (US); Thach Duong, Tustin, CA (US); Jawahar M. Ali, Lake Forest, CA (US); David J. Battles, Santa Barbara, CA (US); Paul W. Mikus, Trabuco Canyon, CA (US); Jay J. Eum, Irvine, CA (US)

(73) Assignee: ENOCARE, Inc., Austin, TX (US)

( * ) Notice: Subject to any disclaimer, the term of this patent is extended or adjusted under 35 U.S.C. 154(b) by 1415 days.

This patent is subject to a terminal disclaimer.

(21) Appl. No.: 12/025,619

(22) Filed: Feb. 4, 2008
(Under 37 CFR 1.47)

(65) Prior Publication Data
US 2008/0154253 A1    Jun. 26, 2008

Related U.S. Application Data

(63) Continuation of application No. 10/700,326, filed on Nov. 3, 2003, now Pat. No. 7,363,071, which is a continuation-in-part of application No. 10/307,036, filed on Nov. 27, 2002, now Pat. No. 6,643,535, which (Continued)

(51) Int. Cl.
*A61B 18/02* (2006.01)
*A61B 8/08* (2006.01)
(Continued)

(52) U.S. Cl.
CPC . *A61B 18/02* (2013.01); *A61B 8/08* (2013.01); *A61B 2017/00084* (2013.01); *A61B 2017/00274* (2013.01); *A61B 2017/3411* (2013.01); *A61B 2018/00547* (2013.01)

(58) Field of Classification Search
USPC ............................. 606/20–21, 22–26
See application file for complete search history.

(56) References Cited

U.S. PATENT DOCUMENTS

| 4,565,200 A | 1/1986 | Cosman |
| 4,672,963 A | 6/1987 | Barken |

(Continued)

FOREIGN PATENT DOCUMENTS

| WO | WO98/23214 | 6/1998 | |
| WO | WO 9823214 A1 * | 6/1998 | ............. A61B 17/34 |

OTHER PUBLICATIONS

Onik, Ultrasound-Guided Cryosurgery, Scientific American at 62 (Jan. 1996).

(Continued)

*Primary Examiner* — Adam Avigan
(74) *Attorney, Agent, or Firm* — Lawrence N. Ginsberg (57) ABSTRACT

The system for providing computer guided ablation of tissue of a patient includes an ablative surgical computer system and a set of surgical devices. The ablative surgical computer system includes a guidance module for providing a treatment guidance plan to an operator; and, a treatment module for acquiring and processing surgical device output data, for optimally controlling treatment parameters and providing feedback information to the operator based on the treatment guidance plan. The set of surgical devices includes at least one ablative device for providing ablation of the treatment region based on the treatment parameters and operator input; and, at least one temperature sensing device for acquiring temperature data from the treatment region and providing a temperature sensing device output signal. The temperature sensing device output signal is a portion of the surgical device output data. The treatment guidance plan is utilized for placing the ablative device and the temperature sensing device into the treatment region.

27 Claims, 9 Drawing Sheets

Related U.S. Application Data is a continuation-in-part of application No. 09/957,306, filed on Sep. 20, 2001, now Pat. No. 6,544,176, which is a continuation of application No. 09/699,938, filed on Oct. 30, 2000, now Pat. No. 6,485,422, which is a continuation of application No. 09/318,710, filed on May 26, 1999, now Pat. No. 6,139,544.

(51) Int. Cl.
    *A61B 17/00*     (2006.01)
    *A61B 17/34*     (2006.01)
    *A61B 18/00*     (2006.01)

(56) References Cited

U.S. PATENT DOCUMENTS

| | | | |
|---|---|---|---|
| 4,776,334 A | 10/1988 | Prionas | |
| 5,222,953 A | 6/1993 | Dowlatshahi | |
| 5,334,181 A * | 8/1994 | Rubinsky et al. | 606/22 |
| 5,454,371 A | 10/1995 | Fenster | |
| 5,494,039 A | 2/1996 | Onik | |
| 5,531,742 A | 7/1996 | Barken | |
| 5,562,095 A | 10/1996 | Downey | |
| 5,647,868 A | 7/1997 | Chinn | |
| 5,706,810 A | 1/1998 | Rubinsky | |
| 5,800,487 A | 9/1998 | Mikus | |
| 5,827,204 A | 10/1998 | Grandia | |
| 5,865,788 A | 2/1999 | Edwards | |
| 5,882,306 A | 3/1999 | Ramamurthy | |
| 5,897,495 A | 4/1999 | Aida | |
| 5,899,860 A | 5/1999 | Pfeiffer | |
| 5,910,104 A | 6/1999 | Doback | |
| 5,976,092 A | 11/1999 | Chinn | |
| 5,978,697 A | 11/1999 | Maytal | |
| 6,071,280 A | 6/2000 | Edwards | |
| 6,083,166 A | 7/2000 | Holdaway | |
| 6,095,975 A | 8/2000 | Silvern | |
| 6,129,670 A | 10/2000 | Burdette | |
| 6,139,544 A * | 10/2000 | Mikus et al. | 606/21 |
| 6,190,378 B1 | 2/2001 | Jarvinen | |
| 6,235,018 B1 | 5/2001 | LePivert | |
| 6,241,725 B1 | 6/2001 | Cosman | |
| 6,248,101 B1 | 6/2001 | Whitmore | |
| 6,256,529 B1 * | 7/2001 | Holupka et al. | 600/427 |
| 6,306,129 B1 | 10/2001 | Little | |
| 6,311,084 B1 * | 10/2001 | Cormack et al. | 600/411 |
| 6,423,009 B1 | 7/2002 | Downey | |
| 6,539,247 B2 | 3/2003 | Spetz | |
| 6,767,346 B2 | 7/2004 | Bui | |
| 6,865,412 B2 | 3/2005 | Dowlatshahi | |
| 6,936,045 B2 | 8/2005 | Yu | |
| 6,958,062 B1 | 10/2005 | Gough | |
| 7,036,516 B1 | 5/2006 | Dees | |
| 7,167,741 B2 | 1/2007 | Torchia | |
| 7,171,255 B2 | 1/2007 | Holupka | |
| 7,171,257 B2 | 1/2007 | Thomson | |
| 7,172,589 B2 | 2/2007 | Lafontaine | |
| 7,189,227 B2 | 3/2007 | Lafontaine | |
| 7,189,228 B2 | 3/2007 | Eum | |
| 7,195,625 B2 | 3/2007 | Lentz | |
| 7,204,833 B1 | 4/2007 | Osorio | |
| 7,207,985 B2 | 4/2007 | Duong | |
| 7,207,986 B2 | 4/2007 | Abboud | |
| 2002/0016540 A1 | 2/2002 | Mikus | |
| 2002/0022832 A1 | 2/2002 | Mikus et al. | |
| 2002/0022869 A1 | 2/2002 | Hareyama | |
| 2007/0010738 A1 | 1/2007 | Mark | |
| 2007/0021741 A1 | 1/2007 | Abboud | |
| 2007/0032783 A1 | 2/2007 | Abboud | |
| 2007/0043342 A1 | 2/2007 | Kleinberger | |
| 2007/0049912 A1 | 3/2007 | Damasco | |
| 2007/0088247 A1 | 4/2007 | Bliweis | |
| 2007/0093799 A1 | 4/2007 | Abboud | |

OTHER PUBLICATIONS

Onik, Cohen, et al. Transrectal Ultrasound-Guided Percutaneous Radical Cryosurgical Ablation of the Prostate, 72 Cancer 1291 (1993).

Wong, et al. Cryosurgery as a Treatment for Prostate Carcinoma, 79 Cancer 963 (Mar. 1997).

Endocare, Cryocare Surgical System 400 Series Operator's Manual (Nov. 2001).

* cited by examiner

SYSTEM FOR PROVIDING COMPUTER GUIDED ABLATION OF TISSUE

CROSS REFERENCE TO RELATED APPLICATIONS

This application is a continuation of U.S. Ser. No. 10/700,326 entitled "Computer Guided Ablation of Tissue Using Integrated Ablative/Temperature Sensing Devices", filed Nov. 3, 2003, which is a continuation in part of U.S. Ser. No. 10/307,036; (now U.S. Pat. No. 6,643,535) entitled "System For Providing Computer Guided Ablation of Tissue", filed Nov. 27, 2002, which is a continuation in part of U.S. Ser. No. 09/957,306, (now U.S. Pat. No. 6,544,176) entitled "Computer Guided Cryosurgery", filed Sep. 20, 2001, which is a continuation of U.S. Ser. No. 09/699,938, (now U.S. Pat. No. 6,485,422) entitled "Computer Guided Cryosurgery", filed Oct. 30, 2000, which is a continuation of U.S. Ser. No. 09/318,710 (now U.S. Pat. No. 6,139,544) entitled "Computer Guided Cryosurgery", filed May 26, 1999.

BACKGROUND OF THE INVENTION

1. Field of the Invention

The present invention relates to cancer surgery and more particularly to a computer guided system for ablative surgery with enhanced feedback.

There is reference in the prior art to the use of computer control systems for providing and/or enhancing cryosurgical techniques. For example, U.S. Pat. No. 4,672,963, issued to I. Barken, discloses an automated and integrated system including a cryosurgery device, an imaging probe and a computer system for use in performing internal surgery.

U.S. Pat. No. 5,647,868, issued to D. O. Chinn, discloses another cryosurgical integrated control and monitoring system.

U.S. Pat. No. 6,139, 544, issued to P. W. Mikus et al, discloses a system for assisting surgeons in performing cryosurgery of the prostate by calculating optimal positions for cryoprobes and providing display based templates for overlay over an ultrasound image display, and displaying actual cryoprobe ultrasound images together with template images so that the surgeon may compare suggested and actual placement of the cryoprobes, and adjust placement accordingly.

The presently utilized CryoCare® Surgical System which is currently manufactured and marketed by Endocare, Inc., Irvine, Calif., utilizes cryoprobes to deliver cold temperatures to the targeted tissue and temperature probes (marketed under the trademark TempProbe®) to monitor temperatures in the surrounding tissue. The CryoCare® Surgical System presently requires a certain degree of skill for operation since the physician requires an understanding of the temperature mapping of the cryoprobes in order to operate them to deliver an effective treatment.

SUMMARY OF THE INVENTION

The present invention is a system for providing computer guided ablation of tissue of a patient. The system includes, in a broad aspect, an imaging device, an ablative surgical computer system, and a set of surgical devices. The imaging device receives imaging data from a treatment region of a patient, processes the imaging data and provides imaging output data and imaging signals. The imaging output data is available to an operator. The ablative surgical computer system includes a guidance module for processing the imaging signals and providing a treatment guidance plan to the operator; and, a treatment module for acquiring and processing surgical device output data, for optimally controlling treatment parameters and providing feedback information to the operator based on the treatment guidance plan. The set of surgical devices includes at least one ablative device for providing ablation of the treatment region based on the treatment parameters and operator input; and, at least one temperature sensing device for acquiring temperature data from the treatment region and providing a temperature sensing device output signal. The temperature sensing device output signal is a portion of the surgical device output data. The treatment guidance plan is utilized for placing the ablative device and the temperature sensing device into the treatment region.

The feedback described above provides enhanced automation and minimizes the potential for operator error resulting in an ineffective or unsuccessful treatment. This enhancement to the CryoCare® Surgical System, discussed above, will be marketed by the present assignee, Endocare, Inc., under the trademark AutoFreeze®.

DETAILED DESCRIPTION OF THE INVENTION

Figure 1:
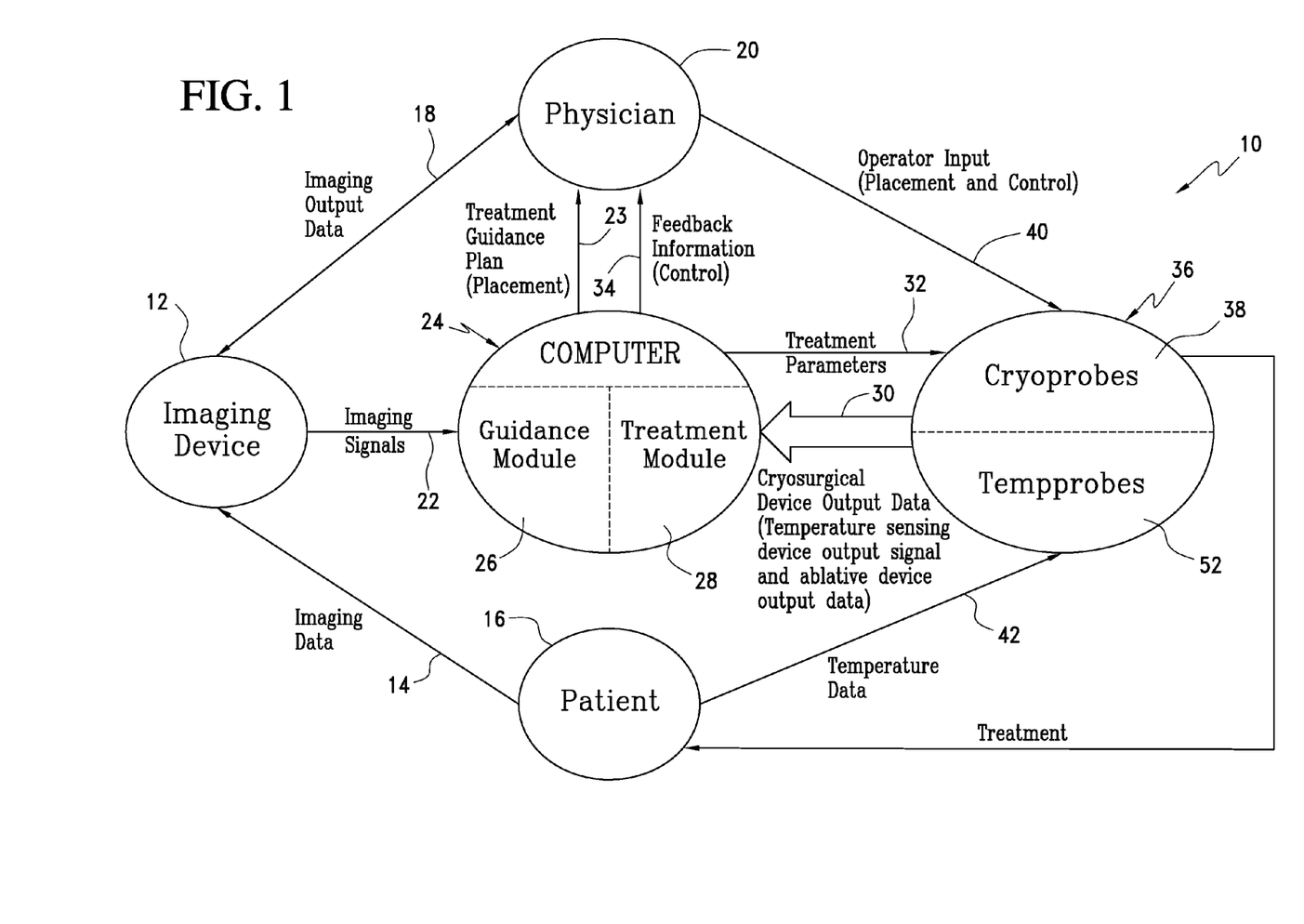
FIG. 1 is an overall system schematic of the present invention.

Referring now to the drawings and the characters of reference marked thereon, FIG. 1 illustrates a preferred embodiment of system for providing computer guided ablation of tissue, of the present invention, designated generally as 10. The system 10 includes an imaging device 12, such as ultrasound, MRI, CT, PET, SPECT, X-ray (including fluoroscope) or other suitable imaging device. The imaging device 12 receives imaging data 14 from a treatment region of a patient 16. The treatment region may be, for example, the prostate region, breast region, liver region, etc. The imaging device 12 provides imaging output data 18 to the physician or other operator 20 and imaging signals 22 to an ablative surgical computer system, designated generally as 24.

The ablative surgical computer system 24 includes a guidance module 26 for processing the imaging signals 22 and providing a treatment guidance plan 23 to the operator 20. The computer system 24 also includes a treatment module 28 for acquiring and processing surgical device output data 30, for optimally controlling treatment parameters 32 and providing feedback information 34 to the operator 20 based on the treatment guidance plan 23.

A set of surgical devices, designated generally as 36, includes at least one ablative device 38 for providing ablation of the treatment region based on the treatment parameters 32 and operator input 40. The set 36 of surgical devices also includes at least one temperature sensing device 52 for acquiring temperature data 42 from the treatment region of the patient 16. The set 36 of surgical devices provides the surgical device output data 30. A temperature sensing device output signal is provided which is a portion of the surgical device output data 30.

In a primary application of the present invention the ablative devices 38 are cryosurgical probes, as will be explained in detail below. However, it is understood that various other types of ablative devices 38 may be used in accordance with the principles of the present invention to provide the necessary ablation. The ablative devices 38 may comprise, for example, radio frequency electrodes, laser fibers, microwave catheters, high-intensity focused ultrasound, and other suitable ablative devices.

Figure 2:
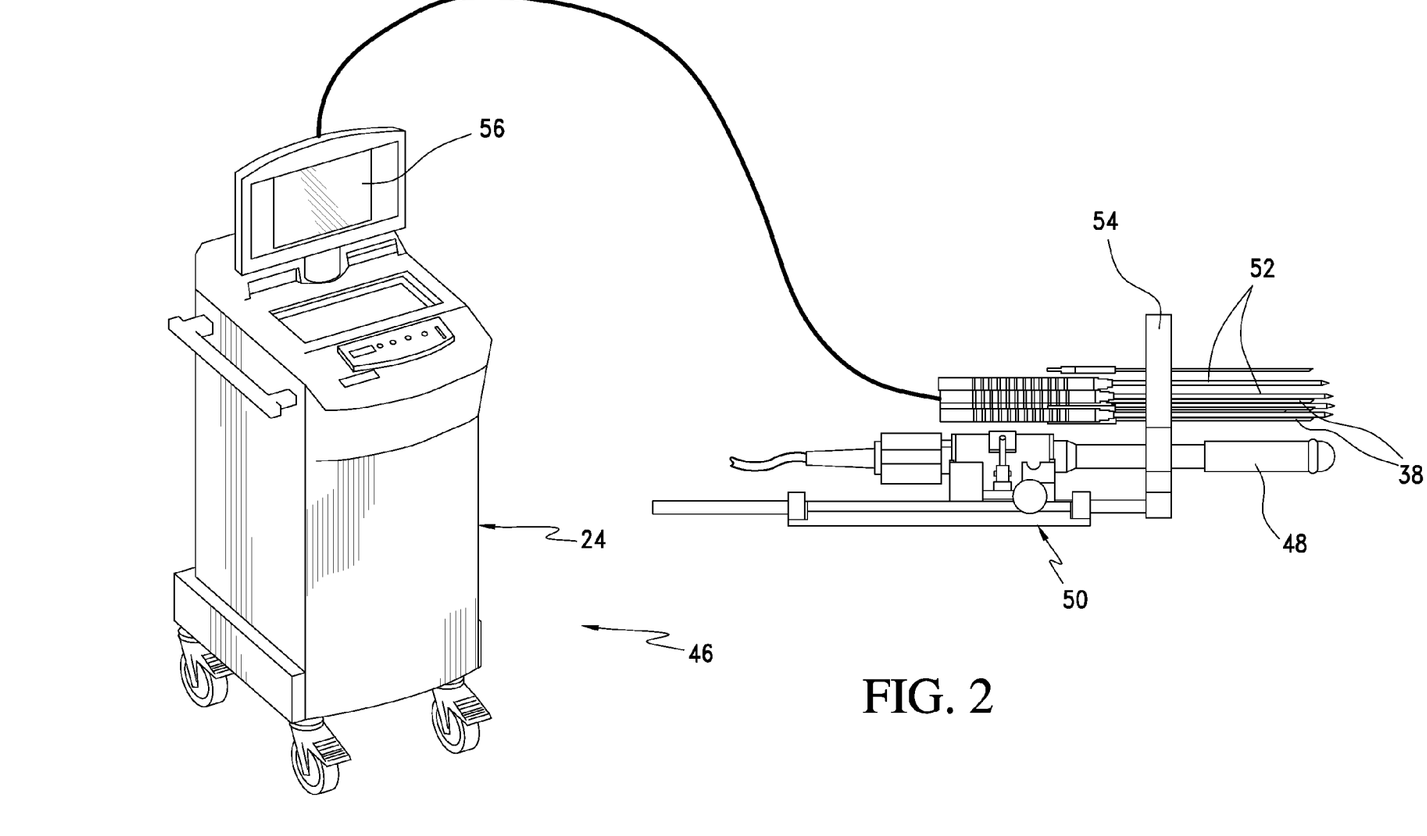
FIG. 2 is a schematic perspective view, partially in cross section of the components of the system for providing computer guided ablation, of the present invention.

Referring now to FIG. 2 utilization of the present system with ablative devices 38, for example, cryosurgical probes, which function to ablate tissue, is illustrated, designated generally as 46. The surgical computer system 24, in present applicants' present application provides guidance as to recommended ablative element placement within a prostate 13, based on images of the prostate acquired from the imaging system, such as an ultrasound system, designated generally as 48.

The computer system 24 is programmed with software capable of: determining the dimensions of the prostate; determining the dimensions of a treatment zone; and, utilizing the determined dimensions of the prostate and treatment zone for computing the number and location of ablative elements needed to treat the treatment zone. An IBM-compatible microprocessor serves as the host computer.

The transrectal ultrasound probe 48 is used to visualize the prostate and the cryosurgical probes. A stepper assembly 50 provides the required advance. The ablative devices (e.g. cryoprobes 38) are illustrated as well as temperature probes 52. The set of surgical devices, i.e ablative devices and temperature sensing devices, are introduced through a grid (i.e. reference plate) 54.

Treatment planning preferably includes the following steps:

Step 1

Capturing Image

The live ultrasound image is displayed in the ultrasound image window.

A button entitled CAPTURE will appear at the bottom of the display.

A brachy-type grid, i.e. grid having an orthogonal reference system, should be displayed on the ultrasound image before the first image is captured.

Using the Capture window, click CAPTURE to capture the first image at the widest cross section of the prostate. Once CAPTURE is selected, the image will be frozen and displayed as a thumbnail image on the right-hand side of the screen.

You can now remove the brachy grid display for the remaining captures.

At least one image is captured. However, there is an option, for example, to capture two images at the widest portion of the prostate gland, one with the brachy grid displayed and one without it displayed, then capture additional images at the base and apex of the gland.

Step 2

Calibration

Typically, there is a calibration step.

Step 3

Outlining

You are asked to click on the four outer points of the prostate image displayed.

Start by clicking on the top edge of the prostate.

Next click on the outer most right hand side of the prostate.

Repeat this action on the bottom edge and left hand outer edge of the prostate as directed in the step 3 window text and illustrations.

When you have clicked on all four points, click the right mouse button to complete the outline.

At anytime during the outlining process, the UNDO button in the step 3 window can be selected to remove the last point placed.

When the prostate outline is completed, the system will move to the URETHRA contour mode.

To outline the urethra click on the center of the urethra and a circle will be placed.

You can adjust the urethra contour location by clicking in the center of the circle and dragging the circle to a new location holding the mouse button down.

You can adjust the size of the urethra outline by clicking on one of the four white dots displayed outside of the outline and moving it inward to reduce the size or pulling it outward to increase the size.

You must click the right mouse button to complete the urethral outline.

When the urethra outline is completed, the system will move to the RECTAL WALL contour mode.

To outline the rectal wall, click on the left top edge of the rectal wall and then click on the right top edge of the rectal wall.

You can adjust the rectal wall outline by clicking on any of the points in the outline and dragging them to a different location.

When the rectal wall outline is complete, right click to move to the next step.

Three image option:

When all outlines on the first image are complete, the system will ask you to outline the urethra on the base and apex images.

Outline the urethra in each additional image using the same method described previously.

Right click each time an outline has been completed.

Figure 3:
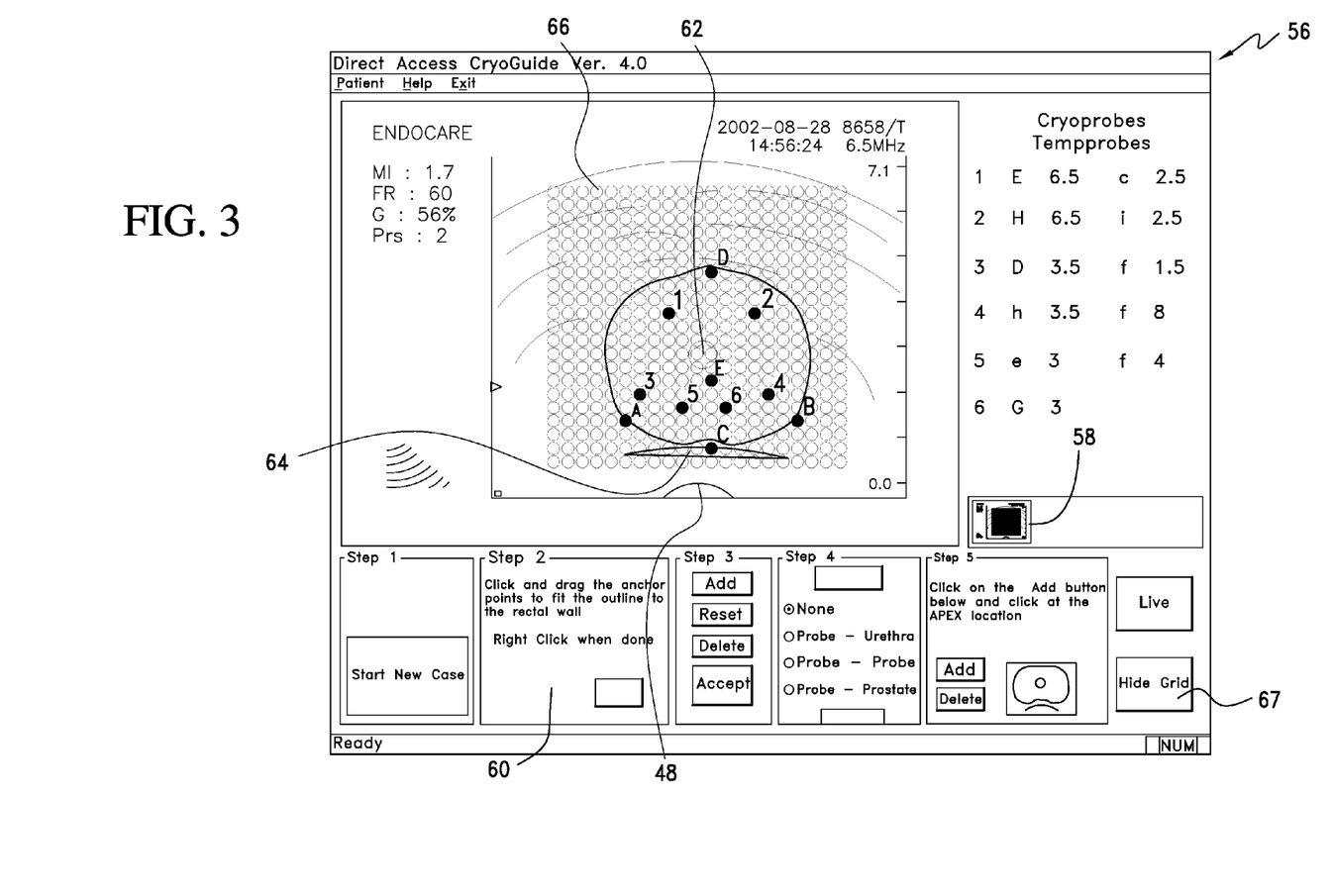
FIG. 3 is a sample display screen of the computer system of the present invention.

Referring now to FIG. 3, a sample display screen, designated generally as 56, of the computer system 24 showing treatment planning is illustrated. The display screen 56 contains various sections. For example, a thumbnail section 58 displays thumbnail images.

Another section on the display screen 48 is the instruction box 60 that provides the user with detailed instructions at each step and makes the system easier to use. Additionally, the system has controls for specifying the patient details (name, age, etc.), calibration, adding/deleting probes and for the simulation of the ablation. The system also provides a pull down menu for switching rendering views and to toggle the display of the probe placements.

Step 4

Placing Probes

The step 4 window and suggested probe placement will appear next to the step 3 window when the outlining is complete. This window allows you to move, add or delete probes if desired.

Probe grid coordinates will also be displayed on the far right hand side of the screen.

To move a probe from the suggested probe placement, click and drag the probe points displayed on the image. This will result in the probe coordinates changing to the new location.

To add or delete probes, click the add or delete button and then click on the location on the image where you want to add a probe or click on the probe you want to delete. This will add or remove the probe to the coordinate display on the right hand side of the screen.

Once the probes are in the desired locations, click on the accept button to proceed to step 6.

Step 5

Measure

This enables the user to display key distance measurements as well as view customized measurement distances.

Step 6

TempProbe® Temperature Probe Placement

Step 6 allows the user to place a TempProbe® temperature probe in the desired location on the image and displays the grid coordinate points that correspond to that placement.

The user is prompted to click on the locations for the right neurovascular bundle (RNVB), left neurovascular bundle (LNVB), Apex and External Sphincter (ES) temperature probes in the image.

For each placement the user must click on the add button in the step 6 window and then click on the location for placement in the image.

A minimum of four temperature probes should be placed.

TempProbe® grid coordinates are displayed on the right hand side of the screen next to Cryoprobe coordinates.

The user can click on the LIVE button in the bottom right hand corner of the screen to overlay the probe placement locations and grid on top of the live ultrasound image.

The user can click on the same button that is now labeled captured images to return to the captured image display.

The user can click on the Hide Grid/Display Grid button in the bottom right hand corner of the screen to toggle the Cryogrid overlay on and off.

Although the aforementioned treatment planning and placement steps have been described with reference to a drag ball or mouse interface device, it is understood that other interface devices can be used such as touch screens, joysticks, etc.

The ultrasound probe image 48 can be seen in FIG. 3. Furthermore, parts of the anatomy can be seen, such as the urethra 62 and the rectum 64. The temperature probes are denoted A, B, C, D and E. The cryoprobes are denoted by numeral designations 1-6. The grid being used is also shown in this display, as denoted by numeral designation 66. As noted above, the grid 66 can, optionally be deleted from the display by selecting the "hide grid" option 67.

Figure 4:
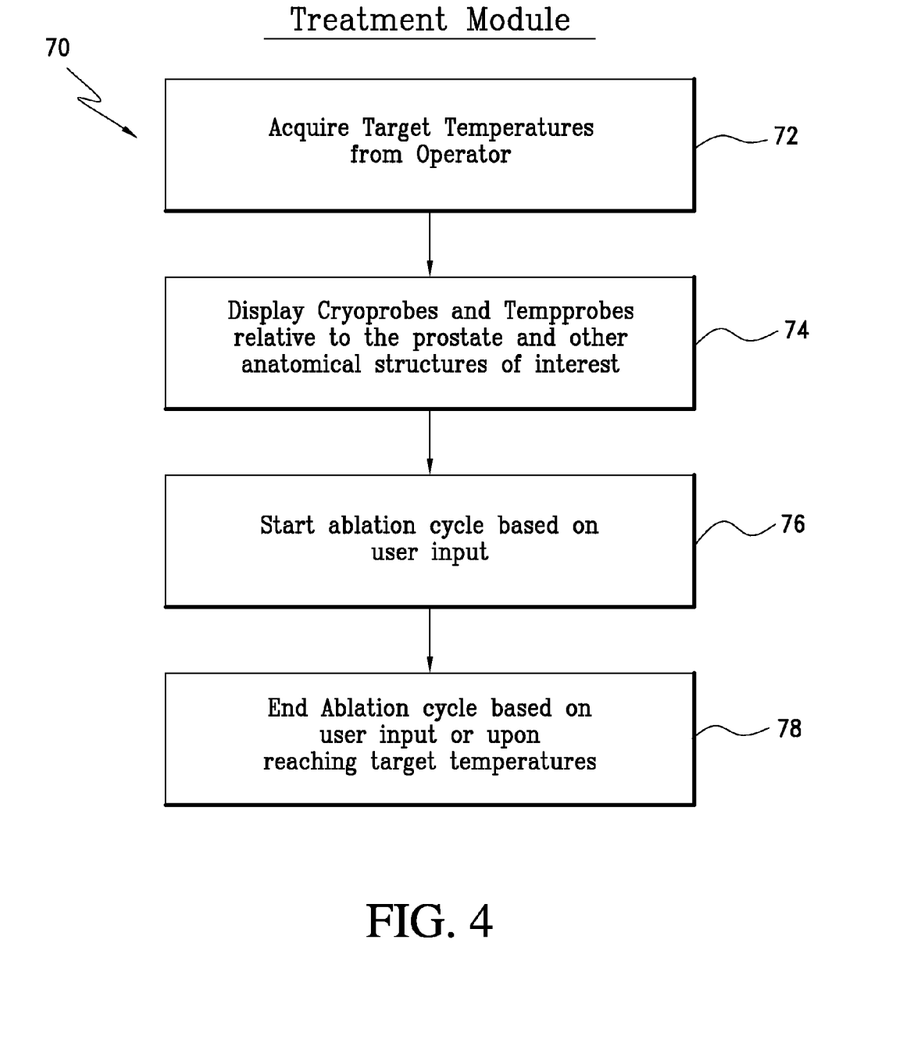
FIG. 4 is a flow diagram of the treatment module of the present invention.

Referring now to FIG. 4, a flow diagram for the treatment module 70, is illustrated. Once the treatment planning has been completed the treatment module 70 is used by the operator to deliver the treatment to the patient. The system provides a user interface for the operator to enter the target temperatures for the treatment of the patient. Each of the temperature probes are therefore assigned a target temperature which is then used to determine the operation of the ablative devices.

Figure 5:
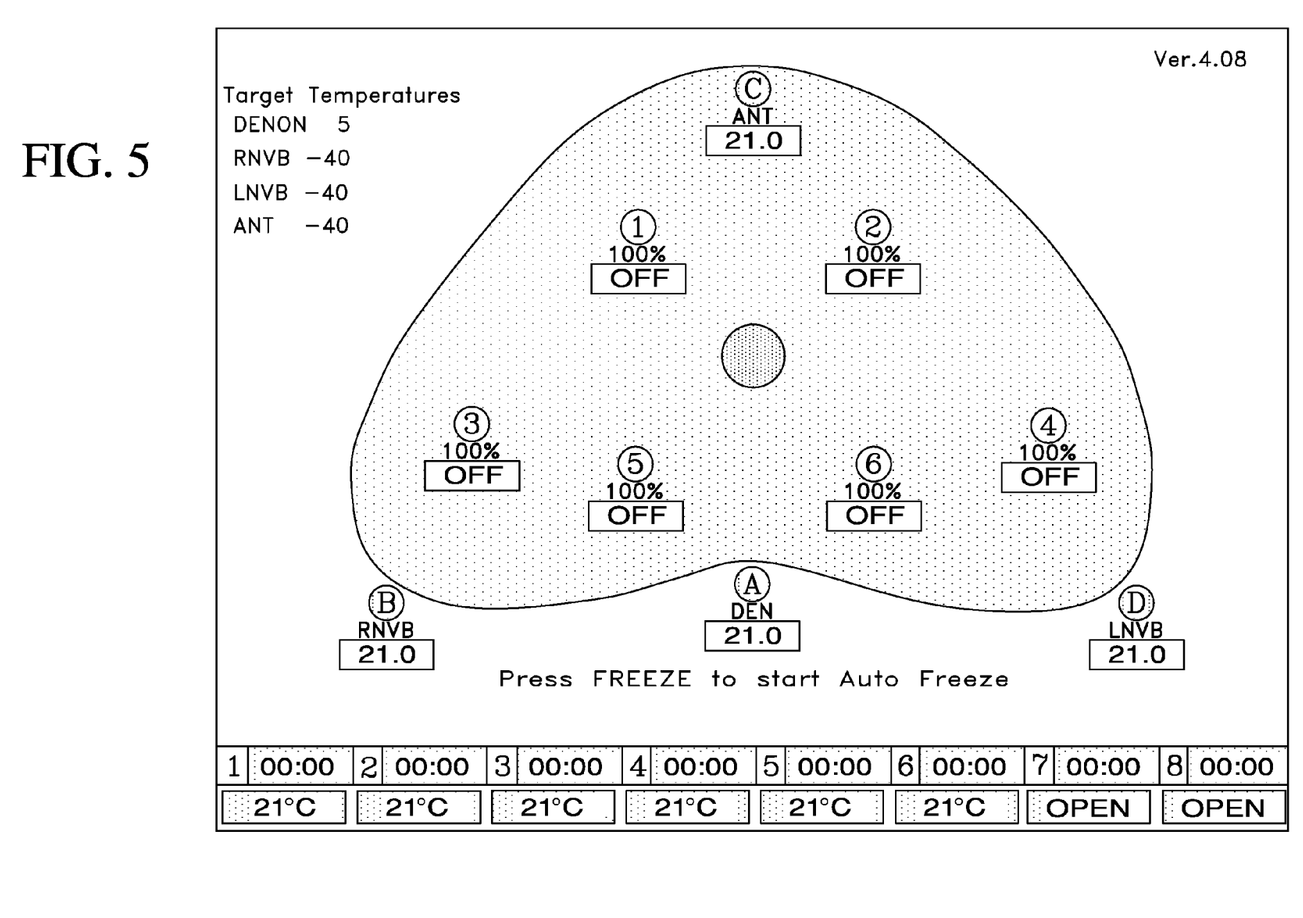
FIG. 5 is an illustration of the prostate showing cryoprobe and temperature probe placement.

Referring to FIG. 5, the cryoprobes and temperature probes are displayed relative to the prostate and other anatomical structures of interest. The target temperatures for each of the temperature probes are also displayed. The cryoprobes are numbered 1-6 in this figure. The temperature probes are designated A-D.

Referring again to FIG. 4, the step of displaying the cryoprobes and temperature probes is denoted by block 74. The ablation cycle is started based on user input (block 76). The ablation cycle is ended, based on user input (block 78) or upon reaching target temperatures.

Figure 6:
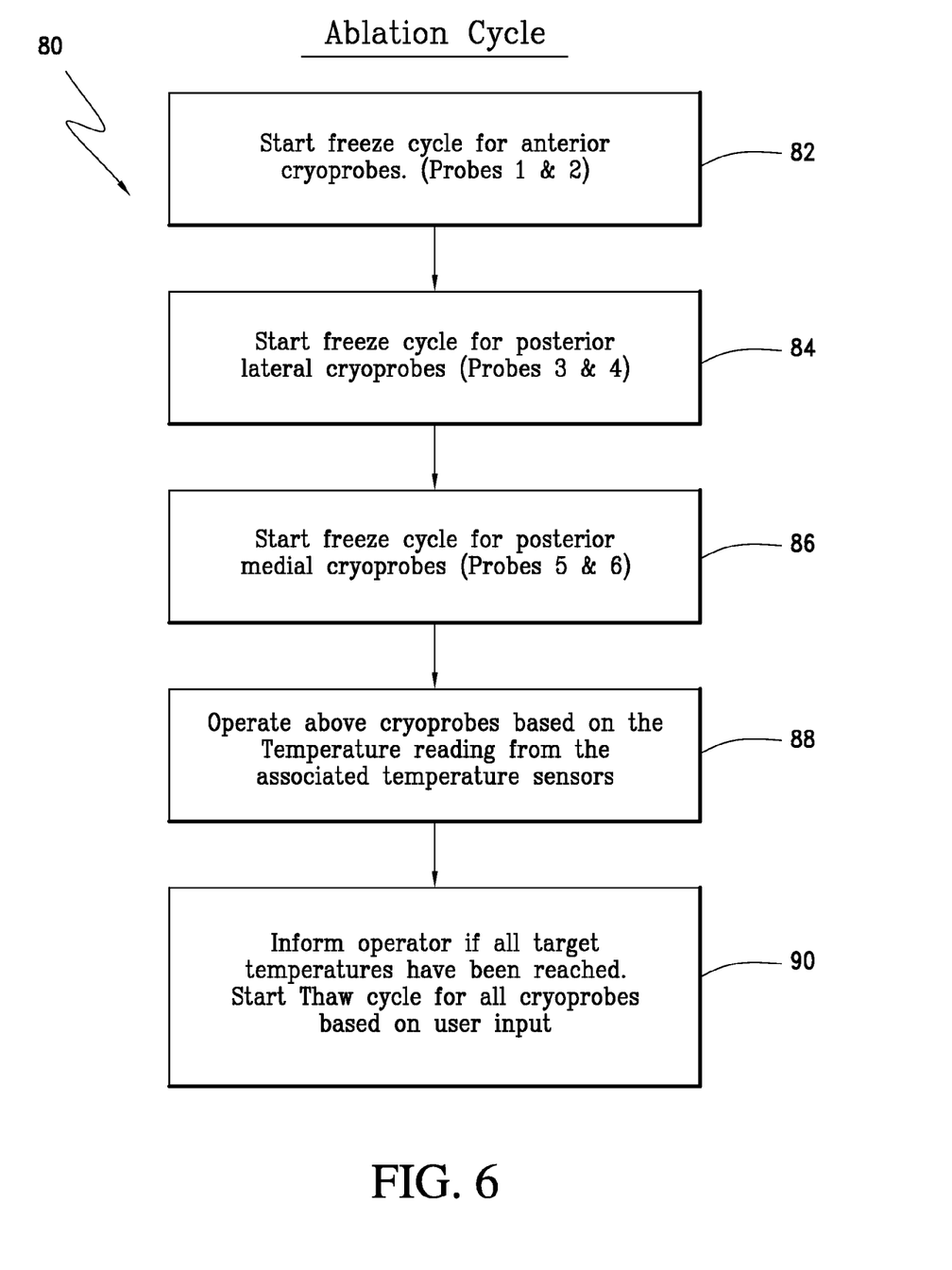
FIG. 6 is a flow diagram of the overall ablation cycle of the present invention.

Referring now to FIG. 6, a flow diagram of the ablation cycle is illustrated, designated generally as 80. A freeze cycle is started for a first anterior cryoprobe and a second anterior cryoprobe, i.e. probes 1 and 2 (block 82). A freeze cycle is started for a first posterior lateral cryoprobe and a second posterior lateral cryoprobe, i.e. probes 3 and 4 (block 84). A freeze cycle is started for a first posterior medial cryoprobe and a second posterior lateral cryoprobe, i.e. probes 5 and 6 (block 86). The cryoprobes are operated based on the temperature data from the temperature sensing devices, i.e. temperature probe in (block 88). The operator is informed if all target temperatures have been reached (block 90). A thaw cycle is started for the cryoprobes based on operator input.

Figure 7A:
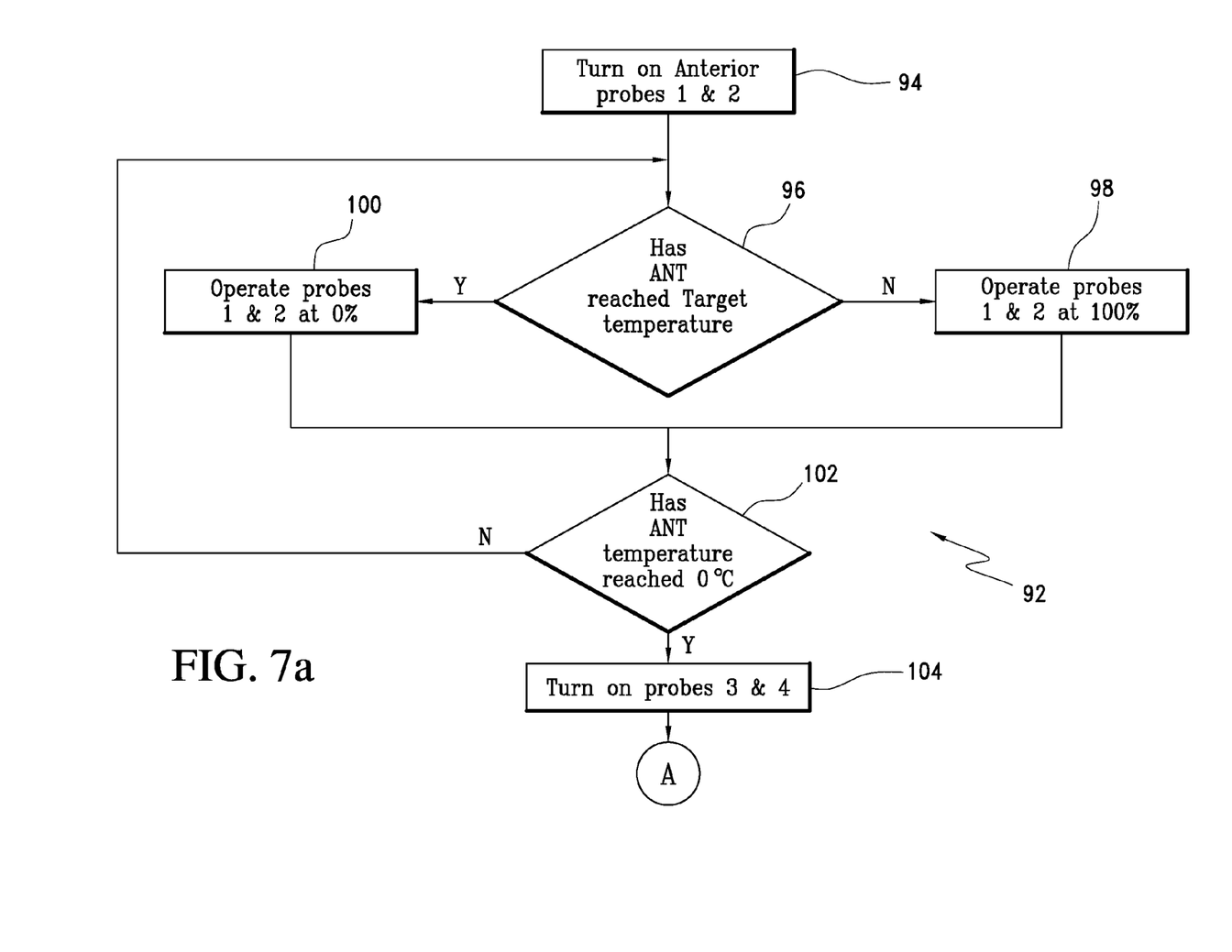
FIG. 7a is flow diagram of the freeze cycle for the first anterior cryoprobe and the second anterior cryoprobe.

Referring now to FIG. 7*a*, the freeze cycle for the first anterior cryoprobe and the second anterior cryoprobe is illustrated, designated generally as 92. It involves the following steps:

a) turning on the first anterior cryoprobe and the second anterior cryoprobe (block 94);

b) determining if an anterior target temperature has been reached (block 96);

c) operating the first anterior cryoprobe and the second anterior cryoprobe at a maximum rate if an anterior target temperature has not been reached (block 98);

d) operating the first anterior cryoprobe and the second anterior cryoprobe at a substantially zero rate if an anterior target temperature has been reached (block 100); and, e) determining if the anterior target temperature has reached substantially 0° C. (block 102). If yes, probes 3 and 4 are turned on (block 104).

Figure 7B:
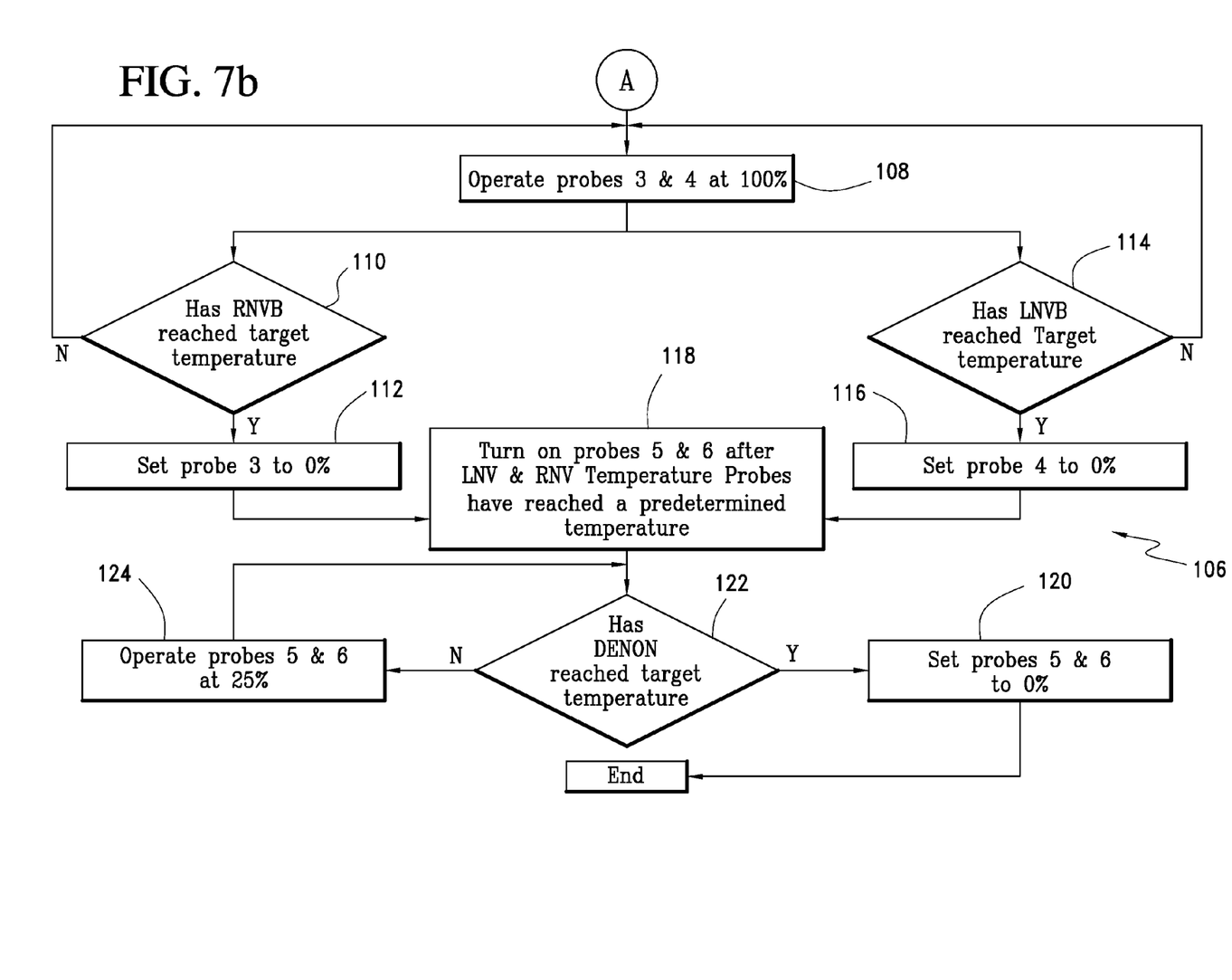
FIG. 7b is a flow diagram of the freeze cycle for the first posterior lateral cryoprobe and the second posterior lateral cryoprobe.

Referring now to FIG. 7*b*, the freeze cycle for the first posterior lateral cryoprobe and the second posterior lateral cryoprobe, and for the first posterior medial cryoprobe and the second posterior lateral cryoprobe, are illustrated, designated generally as 106. These cycles involve the following steps:

a) turning on the first posterior lateral cryoprobe and the second posterior lateral cryoprobe and operating them at a maximum rate (block 108);

b) determining if a first neurovascular bundle target temperature has been reached (block 110);

c) turning off the first posterior lateral cryoprobe if the first neurovascular bundle target temperature has been reached (block 112);

d) determining if a second neurovascular bundle target temperature has been reached (block 114);

e) operating the second posterior lateral cryoprobe at a substantially zero rate if the second neurovascular bundle target temperature has been reached (block 116);

f) turning on the first posterior medial cryoprobe and the second posterior medial cryoprobe after the neurovascular temperature probes are substantially close to their target temperatures (block 118);

g) operating the first posterior medial cryoprobe and the second posterior medial cryoprobe at a power rate in a range of about 15-35%, preferably about 25% (block 124); and, h) setting the first posterior medial cryoprobe and the second posterior medial cryoprobe to a substantially zero rate (block 120) if a Denon Vieller's fascia target temperature has been reached (block 122).

Figure 8:
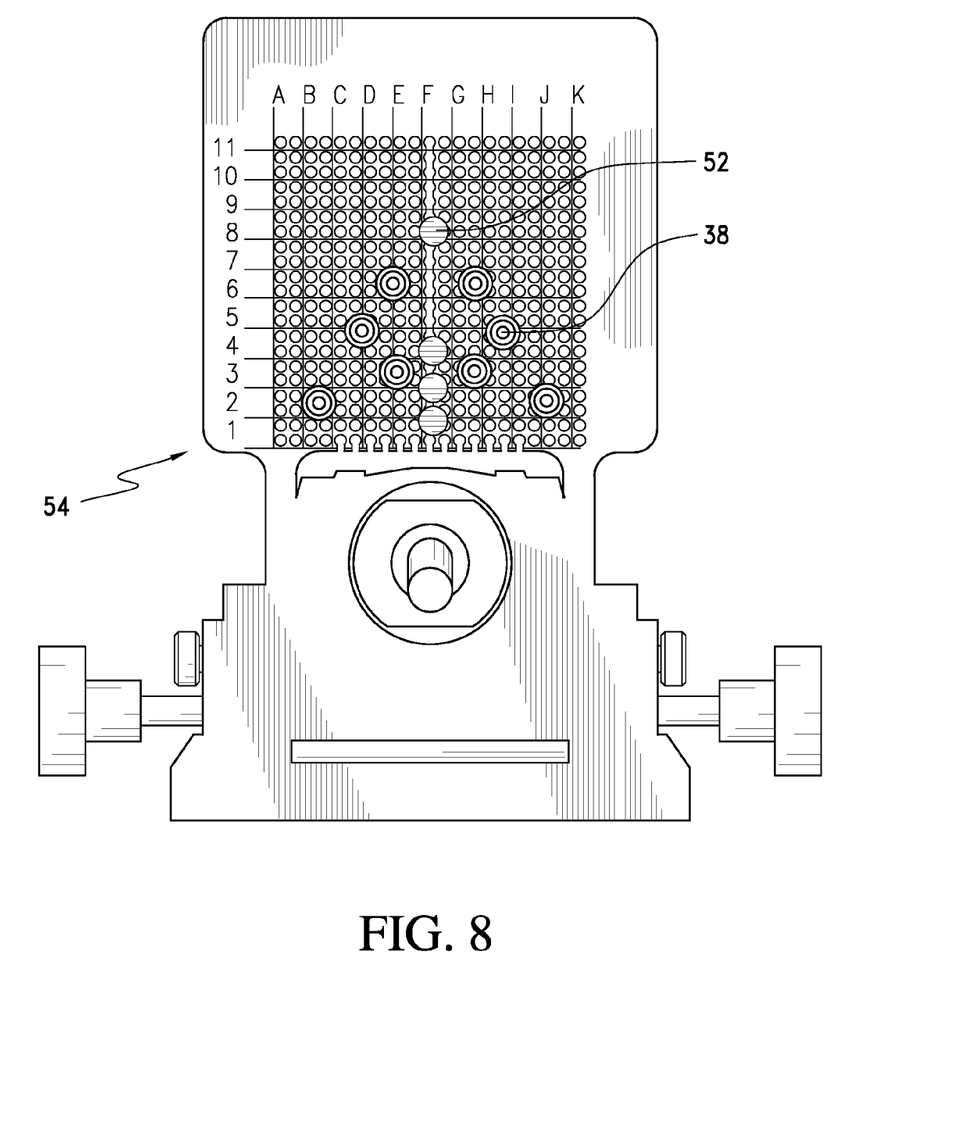
FIG. 8 is a front view of the alignment assembly showing the cryoprobes and temperature probes being placed at selected locations.

Referring now to FIG. 8, an alignment assembly (also referred to as a reference plate, grid or template) is illustrated, designated generally as 54. The alignment assembly 54 utilizes an orthogonal coordinate system to position the cryoprobes and temperature probes. Use of this alignment assembly 54 makes it possible for the cryoprobes and temperature probes to be placed at the locations determined by the guidance module.

The cryoprobes particularly adapted for this computer guided placement are those manufactured by the present assignee, Endocare, Inc., Irvine, Calif. The urethra, which passes through the prostate, is one of the anatomic structures that usually should not be frozen during this surgery. Accordingly, the urethra is protected and kept warm with the urethral warming catheter. The bladder neck sphincter and the external sphincter are also structures that should be protected from freezing, and these are protected from freezing by the warming catheter. A transrectal probe is inserted into the rectum in order to visualize the placement of the probes and the growth of the iceballs formed by the cryoprobes. (As noted above, alternative imaging means may be utilized.) To assist in placement of the cryosurgical probes, a template 21 is used which supports the probes 22 during insertion and while they are installed in the body. The patient is placed in the lithotomic position, i.e. horizontally on an operating table with legs positioned to provide access for the ultrasound probe to be inserted into the rectum and cryoprobes to be inserted through the perineal area into the prostate.

Thus, we have described a system for assisting surgeons in performing cryosurgery of the prostate by calculating optimal positions for cryoprobes and providing display based templates for overlay over an ultrasound image display, and displaying actual cryoprobe ultrasound images together with template images so that the surgeon may compare suggested and actual placement of the probes, and adjust placement accordingly. The method and system is described above in relation to our newly enhanced CRYOCARE® cryosurgical system, which is provided with up to eight independently controlled argon powered cryoprobes. The enhanced CRYOCARE® cryosurgical system utilizes the feedback described above to provide the AutoFreeze® system functionality.

The system cools the probes to cryosurgically effective temperatures (typically below −120° C.) through Joule-Thomson cooling within the probe tips. If used for cryogenic ablation the system may be implemented with other cooling systems such as liquid nitrogen cryoprobes and mixed gas cryoprobes. The placement of probes is calculated based on this system, and the calculations may be adjusted for different systems and numbers of probes. The system may be adapted to other forms of ablation and treatment of the prostate, with adjustments in the calculations being made to account for the ablative range of the devices. Other ablative elements may include, for example, radio frequency devices, microwave devices, high intensity focused ultrasound devices, lasers, radioactive seeds and ablation agents such as chemicals, e.g. alcohol-based substances.

Although the system 10 has been described wherein the physician provides input to start and stop the ablation cycle it is understood that the treatment module may alternatively control the ablative elements automatically based upon a sensing device output signal such as, but not limited to, temperature sensing device measurements, ultrasound images of the rate of ice growth, tissue impedance measurements within the treatment zone. Such a feedback could direct the system to stop the treatment resulting in the system turning off one or more ablative elements automatically without the need for operator intervention.

Thus, while the preferred embodiments of the devices and methods have been described in reference to the environment in which they were developed, they are merely illustrative of the principles of the invention. Other embodiments and configurations may be devised without departing from the spirit of the invention and the scope of the appended claims.

The invention claimed is:

1. A system for providing computer guided ablation of tissue of a patient, comprising:
   a) an imaging device for receiving imaging data from a treatment region of said patient;
   b) an ablative surgical computer system, comprising:
      i. a guidance module for computing a treatment guidance plan that determines a size of the treatment region and based on the size of the treatment region and prior to any simulated ablative device placement by an operator in the guidance module, computes for the operator a recommended number and a recommended placement of the ablative devices to treat the treatment region; and
      ii. a treatment module for optimally controlling treatment parameters and providing feedback information to the operator based on said treatment guidance plan; and
   c) at least one ablative device for providing ablation of the treatment region based on said treatment parameters and operator input.

2. The system of claim 1, wherein the imaging device is configured to process said imaging data and provide imaging output data and imaging signals, said imaging output data being available to the operator.

3. The system of claim 2, wherein said imaging output data comprises visual imaging output data.

4. The system of claim 1, wherein said treatment region comprises a region containing cancerous tissue.

5. The system of claim 1, wherein said treatment guidance plan comprises a plan that provides an optimal placement for the at least one ablative device relative to the treatment region.

6. The system of claim 1, further comprising
   an alignment assembly for placing said at least one ablative device into said treatment region based on said treatment guidance plan.

7. The system of claim 1 wherein said at least one ablative device comprises a plurality of cryosurgical probes.

8. The system of claim 7, wherein said plurality of cryosurgical probes is selected from the group consisting of 2, 3, 4, 5, 6, 7, and 8 cryoprobes.

9. The system of claim 1, wherein said treatment region is a prostate.

10. The system of claim 1, wherein said at least one ablative device is a cryosurgical probe.

11. A method of providing computer guided ablation of target tissue of a patient, comprising the steps of:
   a) receiving imaging data from the patient;
   b) providing a treatment guidance plan to an operator that comprises (i) determining a size of the target tissue and based on the size of the target tissue, and (ii) prior to any simulated ablative device placement by the operator, computing a number of the ablative devices and a placement of the ablative devices to treat the tissues of the patient;
   c) acquiring and processing surgical device output data, for optimally controlling treatment parameters and providing feedback information to the operator based on said treatment guidance plan; and d) operating at least one surgical device, said at least one surgical device providing said surgical device output data, wherein
the at least one surgical device provides ablation of the tissue based on said treatment parameters and operator input.

12. The method of claim 11, further comprising a step of processing said imaging data and providing imaging output data and imaging signals, said imaging output data being available to said operator.

13. The method of claim 11, wherein said step of receiving imaging output data comprises receiving visual imaging output data.

14. The method of claim 11, wherein said target tissue is a prostate.

15. The method of claim 11, wherein said imaging data comprises visual imaging data.

16. The method of claim 11, wherein said target tissue comprises cancerous tissue.

17. The method of claim 11, wherein said treatment guidance plan comprises a plan that provides an optimal placement for the at least one surgical device relative to the target tissue.

18. The method of claim 11, wherein said at least one surgical device is a cryosurgical probe.

19. A system for providing computer guided ablation of target tissue of a patient, comprising:
an ablative surgical computer system, comprising:
i. a first module for (a) processing patient imaging information received from an imaging device and (b) computing a treatment guidance plan that determines a size of the target tissue and based on the size of the target tissue, computes for an operator, prior to any simulated ablative device placement by the operator, a recommended number and a recommended placement of the ablative devices to treat the treatment region; and,
ii. a second module for optimally controlling treatment parameters and providing feedback information to the operator based on said treatment guidance plan; and,
at least one ablative device for providing ablation of the tissue based on said treatment parameters and operator input.

20. The system of claim 19, wherein said at least one ablative device is a cryosurgical probe.

21. The system of claim 19, wherein said target tissue is a prostate.

22. A system for providing computer guided ablation of a treatment region of a patient, comprising:
a computing device configured to (i) process patient imaging information received from an imaging device, (ii) generate a treatment guidance plan that determines a size of the treatment region and based on the size of the treatment region and prior to any simulated ablative device placement by an operator, computes for the operator, a recommended number and a recommended placement of the ablative devices to treat the treatment region, and (iii) control treatment parameters and provide feedback information to the operator based on said treatment guidance plan; and
at least one ablative device for providing ablation of the treatment region based on said treatment parameters and operator input.

23. The system of claim 22, wherein the imaging device is configured to process the imaging data and provide imaging output data and imaging signals, the imaging output data being available to the operator.

24. The system of claim 22, wherein the treatment region comprises cancerous tissue.

25. The system of claim 22, wherein the treatment region is a prostate.

26. The system of claim 22, wherein the at least one ablative device is selected from the group consisting of cryoprobes, radio frequency electrodes, laser fibers, microwave catheters, and high-intensity focused ultrasound devices.

27. The system of claim 22, wherein said imaging device is selected from the group consisting of ultrasound devices, MRI devices, CT devices, PET devices, SPECT devices and X-ray devices.

* * * * *